(12) United States Patent
Thorstenson et al.

(10) Patent No.: US 8,449,527 B2
(45) Date of Patent: May 28, 2013

(54) SPLITTABLE CANNULA HAVING RADIOPAQUE MARKER

(75) Inventors: Chad A. Thorstenson, Andover, MN (US); Richard E. Stehr, Stillwater, MN (US); Omar Amirana, Minneapolis, MN (US); Daniel J. Potter, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 139 days.

(21) Appl. No.: 12/980,973

(22) Filed: Dec. 29, 2010

(65) Prior Publication Data
US 2011/0092911 A1 Apr. 21, 2011

Related U.S. Application Data

(63) Continuation of application No. 11/052,617, filed on Feb. 4, 2005, now Pat. No. 7,879,024, which is a continuation-in-part of application No. 10/609,206, filed on Jun. 26, 2003, now abandoned.

(51) Int. Cl.
*A61M 25/098* (2006.01)

(52) U.S. Cl.
USPC ........................................ 604/529; 604/103.1

(58) Field of Classification Search
USPC ............ 606/194; 604/20, 529, 103.1, 164.05, 604/1.34
See application file for complete search history.

(56) References Cited

U.S. PATENT DOCUMENTS

| | | | |
|---|---|---|---|
| 5,489,277 A * | 2/1996 | Tolkoff et al. | 604/529 |
| 5,968,068 A | 10/1999 | Dehdashtian et al. | |
| 6,277,108 B1 * | 8/2001 | McBroom et al. | 604/529 |
| 6,562,049 B1 * | 5/2003 | Norlander et al. | 606/108 |
| 6,579,311 B1 * | 6/2003 | Makower | 623/1.23 |
| 6,616,626 B2 * | 9/2003 | Crank et al. | 604/48 |
| 7,641,647 B2 * | 1/2010 | Gunderson | 604/529 |
| 2002/0183826 A1 | 12/2002 | Dorn et al. | |
| 2005/0171527 A1 * | 8/2005 | Bhola | 606/41 |

* cited by examiner

*Primary Examiner* — Katherine Dowe
*Assistant Examiner* — Diane Yabut
(74) *Attorney, Agent, or Firm* — Wiley Rein LLP

(57) ABSTRACT

A splittable cannula includes a radiopaque marker placed at or near the distal end of the cannula. The radiopaque marker may be a unitary piece, or may consist of several portions. The cannula may include a sheath or catheter body with a grooved score line running along a portion of the sheath body and a radiopaque marker located at a distal end of the body and abutting the body. The radiopaque marker may be located within the lumen of the sheath, may be embedded in the sheath wall, or may be affixed to the external sheath wall. The radiopaque marker may be scored, notched, grooved, or contain apertures longitudinally. The notches, grooves, apertures, and/or score lines in both the sheath or catheter body and the radiopaque marker serve to provide a weakened tear path. An electrode lead may be coupled with the radiopaque marker.

17 Claims, 9 Drawing Sheets

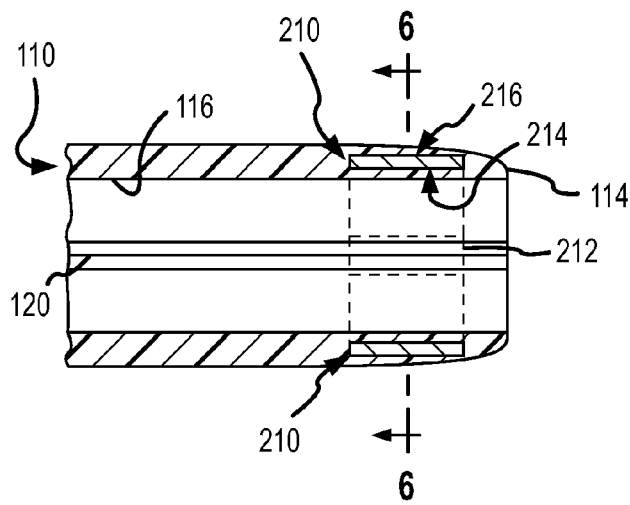
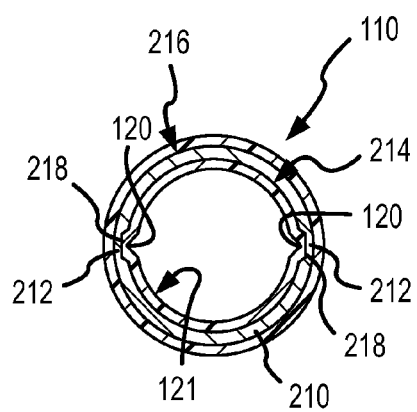
FIG.5    FIG.6
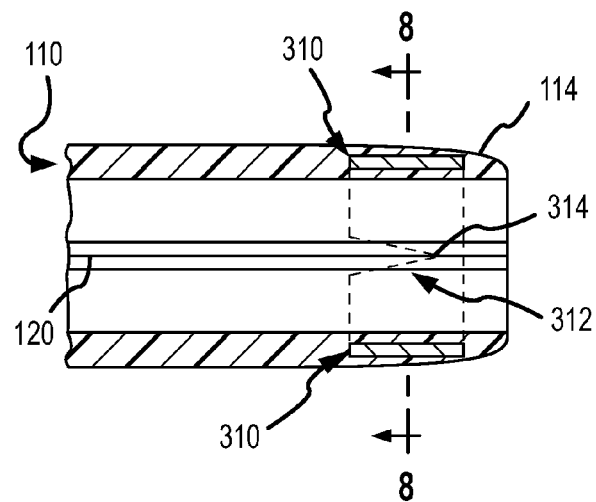
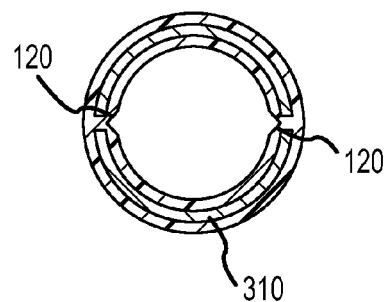
FIG.7    FIG.8

SPLITTABLE CANNULA HAVING RADIOPAQUE MARKER

CROSS REFERENCE TO RELATED APPLICATIONS

This application is a continuation of U.S. application Ser. No. 11/052,617, filed 4 Feb. 2005, now, U.S. Pat. No. 7,879,024, which is a continuation-in-part of U.S. application Ser. No. 10/609,206, filed 26 Jun. 2003, now abandoned. The foregoing applications are hereby incorporated by reference as though fully set forth herein.

BACKGROUND OF THE INVENTION a. Field of the Invention

This invention relates generally to the field of medical instruments, and more particularly to a cannula having a radiopaque portion, for use during medical procedures.

b. Description of the Related Art

Several medical procedures require the introduction of one or more medical instruments into arteries or veins so that the medical instruments may be advanced to a body location requiring, for example, diagnosis or treatment. Various types of cannula, for example, sheaths and catheters, are often introduced into a patient's body to perform medical procedures. The term "sheath" is generally applied to a cannula through which other medical instruments (for example, catheters, guidewires, leads, and dilators) are inserted and introduced within the body for manipulation. When used as a conduit to introduce other medical devices, the cannula is often referred to as an "introducer sheath." The sheath effectively acts as a conduit, preventing damage to the wall of the vein or artery into which it is inserted. Similarly, the sheath may protect the region of the body to be diagnosed and/or treated. A hemostasis valve may be mounted to the proximal end of the sheath located outside the patient's body in order to inhibit leakage of blood flowing through the sheath.

In many medical procedures, the location of the sheath tip is important, insofar as the sheath must extend to the portion of the patient's body being diagnosed or treated. For example, ablation of a patient's heart requires precise placement of a catheter. Oftentimes, the catheter or sheath tip is tracked or located by electrophysiological guidance, fluoroscopy, or a combination of the two. In order to accurately track the distal tip of the catheter with fluoroscopy, a radiopaque material (i.e., a material reflecting or opaque to x-rays) is typically incorporated into the catheter tip in some fashion. The radiopaque material generally takes the form of a coating or solid, metallic ring.

Many times, introducer sheaths or cannulas are also splittable. That is, they may be torn apart longitudinally while removed from a patient's body in order to more rapidly remove the sheath, and thus limit blood loss. However, the radiopaque material often inhibits splitting of the introducer sheath, especially when the radiopaque substance is in the form of a solid metal ring. Even coatings applied to a sheath may reduce the sheath's ability to split apart. Thus, many current introducer sheaths compromise between quick removal and detectability via x-rays during procedures. Accordingly, there is a need for an improved introducer sheath having a radiopaque marker.

The information included in this Background section of the specification, including any references cited herein and any description or discussion thereof, is included for technical reference purposes only and is not to be regarded subject matter by which the scope of the invention is to be bound.

SUMMARY OF THE INVENTION

Generally, one embodiment of the present invention takes the form of a splittable cannula or sheath, suitable for introduction into a blood vessel or other portion of a human body, including a radiopaque marker at its distal end and splittable along its length. As used herein, "proximal" refers to the direction away from the patient and toward the clinician, while "distal" indicates the direction toward the patient and away from the clinician. The sheath may include a sheath body having at least one longitudinally extending sheath score line running along a substantial portion of the sheath body, a substantially cylindrical radiopaque marker located at a distal end of the sheath body and abutting the sheath body, and at least one longitudinally extending marker score line running along a substantial portion of the radiopaque marker. The radiopaque marker may be located within the lumen of the sheath, or may be embedded in the sheath wall. Similarly, alternative embodiments may replace the marker score line with a notch or groove running along the length of the radiopaque marker. The notches, grooves, and/or score lines in both the sheath body and radiopaque marker serve to provide a weakened tear path, thus facilitating rapid removal of the sheath and marker from a patient's body.

Generally, the sheath and marker score lines are substantially aligned, in order to permit relatively simultaneous splitting of the marker and the portion of the sheath surrounding the marker. Where a notch is used in lieu of a marker score line, the notch is typically similarly aligned with a sheath score line. Generally, many (although not necessarily all) embodiments of the cannula and radiopaque marker have two opposing score lines located substantially opposite one another along the sheath and marker bodies. However, the score lines on the cannula and the marker need not be diametrically opposed and may be closer than 180° apart along the shortest arc between the score lines on the outer circumference of the cannula or marker bodies.

In yet another embodiment, the radiopaque marker may be made of two or more discrete radiopaque portions, which may or may not be in direct contact with one another. For example, one embodiment of the radiopaque marker takes the form of two semicircular portions embedded within or affixed to the sheath wall at or near the distal tip. In such an embodiment, neither semicircular portion overlaps or contacts a sheath score line. Instead, the sheath score line or lines run along a gap between the semicircular portions. Accordingly, when the sheath is split, it tears between the radiopaque semicircular portions. This eliminates the need to actually break or tear through radiopaque material.

A further embodiment of the invention is directed to a splittable cannula having a section opaque to x-rays. The splittable cannula may be composed of a tubular body formed by a sidewall, wherein the sidewall further defines a pair of opposing, longitudinally extending grooves. A radiopaque marker is attached to the sidewall. The radiopaque marker has an annular wall with first and second weakened areas in the annular wall. The first weakened area of the annular wall is at a first position on the annular wall and the second weakened area of the annular wall at a second position on the annular wall substantially opposite the first position. The first weakened area and the second weakened area divide the annular wall into substantially equal opposing halves. At least one connecting strip in each of the first and second weakened areas join the opposing halves of the radiopaque marker. The first weakened area is aligned with a first one of the grooves and the second weakened area is aligned with a second one of the grooves.

In one embodiment of the invention, a splittable sheath has a distal end opaque to x-rays. In this embodiment, the splittable sheath is composed primarily of a tubular body and a radiopaque marker. The tubular body is formed by a sidewall and the sidewall further defines a pair of opposing, longitudinally extending grooves. The radiopaque marker is attached to the sidewall and positioned at the distal end of the splittable sheath. The radiopaque marker has an annular wall with a first pair of notches and a second pair of notches in the annular wall. The first pair of notches is at a first position on the annular wall and the second pair of notches is at a second position on the annular wall substantially opposite the first position. Each of the first pair of notches is separated from the other by a first connecting strip. Similarly, each of the second pair of notches is separated from the other by a second connecting strip. The first pair of notches is aligned with a first one of the grooves and the second pair of notches is aligned with a second one of the grooves.

Another embodiment of the invention is also a splittable sheath having a distal end opaque to x-rays. The splittable sheath is again a tubular body formed by a sidewall. The sidewall further defines a pair of opposing, longitudinally extending grooves. A radiopaque marker is attached to the sidewall and positioned at the distal end of the splittable sheath. The radiopaque marker has an annular wall with a first plurality of holes within the annular wall extending longitudinally at a first position on the annular wall. The radiopaque marker also has a second plurality of holes within the annular wall extending longitudinally at a second position on the annular wall substantially opposite the first position. The first plurality of holes is aligned with a first one of the grooves and the second plurality of holes is aligned with a second one of the grooves.

In another embodiment of the invention, a splittable catheter has a distal end opaque to x-rays. The splittable catheter is composed of a tubular body formed by a sidewall. The sidewall further defines a pair of opposing, longitudinally extending grooves. A radiopaque marker electrode is attached to an outer surface of the sidewall and positioned at the distal end of the splittable catheter. An electrode lead is coupled to the radiopaque marker electrode. The radiopaque marker electrode has an annular wall with a first pair of notches and a second pair of notches. The first pair of notches is at a first position on the annular wall and the second pair of notches is at a second position on the annular wall substantially opposite the first position. Each of the first pair of notches is separated from the other by a first connecting strip. Likewise, each of the second pair of notches is separated from the other by a second connecting strip. The first pair of notches is aligned with a first one of the grooves and the second pair of notches is aligned with a second one of the grooves.

A method of manufacturing a splittable sheath having a distal end opaque to x-rays is also disclosed. In this method a distal end of the sheath is held within at least one holding die. An annular slit is cut longitudinally within a sidewall of the sheath at the distal end. Placing either longitudinal end of a radiopaque marker is placed on an insertion tool. At least one marker guide on the insertion tool self-aligns with at least one notch in the radiopaque marker. The insertion tool is oriented with the distal end of the sheath. At least one score guide on the insertion tool aligns with at least one groove on an interior surface of the sidewall of the sheath. The insertion tool is then inserted into a lumen defined by the sidewall at the distal end of the sheath. The radiopaque marker is thereby simultaneously inserted into the annular slit within the sidewall of the sheath.

Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 5 depicts a longitudinal cross-sectional view of a tip of a third embodiment of a splittable introducer sheath incorporating a first embodiment of a radiopaque marker ring.

FIG. 6 depicts a cross-sectional view, taken along line 6-6 of FIG. 5, of the tip of the third embodiment of the introducer sheath, as shown in FIG. 5.

FIG. 7 depicts a longitudinal cross-sectional view of a tip of a splittable introducer sheath incorporating a second embodiment of a radiopaque marker ring.

FIG. 8 depicts a cross-sectional view, taken along line 8-8 of FIG. 7, of the tip of the introducer sheath, as shown in FIG. 7, depicting the second embodiment of the radiopaque marker ring.

DETAILED DESCRIPTION OF THE INVENTION

Figure 1:
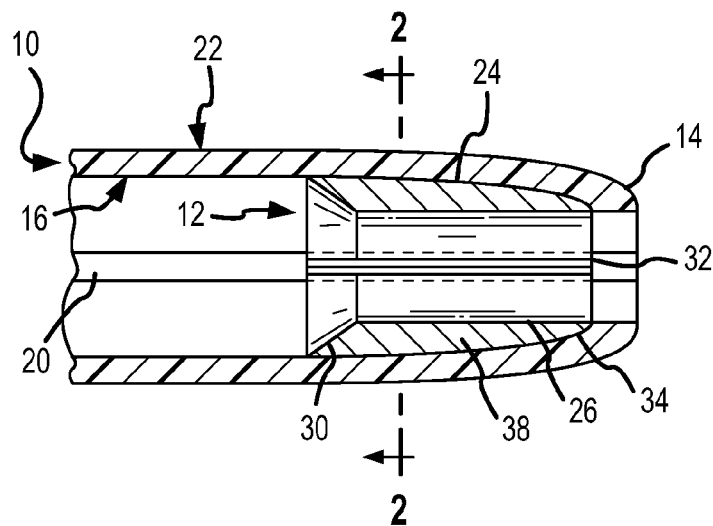
FIG. 1 depicts a longitudinal cross-sectional view of a tip of a first embodiment of a splittable introducer sheath incorporating a radiopaque tube-shaped marker.

One embodiment of the present invention comprises a cannula in the form of a sheath having one or more radiopaque marker materials placed along the tip of sheath. The radiopaque materials generally reflect x-rays, which in turn display the location of the sheath tip on standard monitors in use in hospitals or other operating environments. Such monitoring of the tip location allows a clinician to pinpoint the tip location, which in turn facilitates the general operation for which the sheath is used. As used herein, the term "sheath" is one exemplary embodiment of a "cannula" according to the present invention.

The radiopaque marker may be bonded to the inside wall of the sheath defining a lumen, it may be embedded within the sheath wall, or it may be on the outside wall of the sheath. Further, the radiopaque marker may be a radiopaque material suspended within a polymer, or may be one or more solid, contiguous pieces of material. For example, the radiopaque marker may take the form of fine particles of barium sulfate suspended in a polymer tube, or may be a ring of radiopaque substance bonded to the inner surface of the cannula. Exemplary radiopaque materials suitable for use with the present invention include metals such as platinum, tungsten, gold, bismuth, or other metals opaque to x-rays, or polymeric materials designed to be x-ray opaque.

The sheath may be split along its longitudinal axis to facilitate removal from a patient's body. Such splitting is generally accomplished by scoring or weakening the sidewall of the sheath in order to provide a tear path along the sheath's longitudinal axis. The scoring may be along the inside or outside walls of the sheath, and typically forms a score line. The sheath is typically scored along two lines in the sidewall parallel to the longitudinal axis such that the sheath will split into two separate portions. Generally, the score lines are located substantially opposite one another along the sheath. However, the score lines on the sheath need not be diametrically opposed and may be closer than 180° apart along the shortest arc between the score lines on the outer circumference of the sheath, for example, with an arc length spacing of between 135° and 180°.

When the radiopaque marker takes the form of a single contiguous piece, it may have a variety of cross-sectional shapes designed to facilitate splitting of the sheath. For example, a groove or notch may be provided and aligned with the sheath score lines, in order to reduce the amount of radiopaque material present along the weakened sheath walls. The notch may take a variety of forms, as discussed in greater detail below. Alternatively, the radiopaque marker may be serrated instead of grooved or notched. As with the grooves or notches, serrations may facilitate splitting of the sheath. Accordingly, the term "score line," as used herein, is intended to embrace scores, notches, serrations, walls having reduced cross-sections, and so forth. Again, the score lines are generally located substantially opposite one another about the marker. However, the score lines on the marker need not be diametrically opposed and may be closer than 180° apart along the shortest arc between the score lines on the outer circumference of the marker, for example, with an arc length spacing of between 135° and 180°. Generally, the separation distance between the score lines of the sheath and the score lines of the marker are the same. Further, the score lines of the sheath and the score lines of the marker are aligned such that when the sheath is split longitudinally, the marker will similarly split into two portions, each contained within a respective portion of the sheath.

In an alternate embodiment, the radiopaque material may comprise multiple strips, pieces, or other elements arranged in such a manner as to provide opacity during fluoroscopy or other medical procedures. Such strips may be overlapping or contiguously placed sufficiently close to one another to provide the aforementioned opacity. In alternative embodiments, the radiopaque marker may be formed from a braided material.

Generally, no matter the exact form taken by the radiopaque material (whether particulate, multiple sections, or a single element), the material is sufficiently dense to be opaque when viewed from a variety of angles during fluoroscopy. Further, the radiopaque marker embodiments discussed herein generally extend from the distal end along a portion of the sheath lumen, and may extend along any distance of the lumen, up to and including the entirety of the lumen, in alternative embodiments.

Sheath Having an Radiopaque Marker Attached to the Inner Sheath Wall

Turning now to FIG. 1, a cross-section of a first embodiment of a splittable introducer sheath 10 incorporating a radiopaque marker 12 is depicted. Generally, the sheath 10 is made of a polymer or other material suitable for introduction into a vein, artery, or other portion of a patient's body. The sheath 10 is weakened along its longitudinal axis by at least one score line 20. Generally, such score lines 20 extend substantially from a neck, or other point of attachment to a hemostasis valve (the "proximal end" of the sheath), to the opposite end of the introducer sheath 10 (the "tip" 14 or "distal end" of the sheath). In the cross-section of the embodiment shown in FIG. 1, two score lines run along the interior wall 16 defining the lumen of the sheath 10. Each score line 20 is approximately opposite the other along the interior wall 16 of the sheath 10. (See FIG. 2.) In alternative embodiments, more score lines or grooves may be present, or the score lines may run along the exterior wall 22 of the sheath 10.

Typically, the entire length of the sheath 10 is splittable. This permits the sheath to be divided into multiple, separate portions as it is removed from the patient's body. Although specific reference is made herein to score lines 20, grooves, and/or weakened portions of the sidewall 18 of the sheath 10, any structure permitting the division of the introducer sheath 10 into two or more separate longitudinal pieces is contemplated as being usable with the present invention.

Extending along the interior of the distal portion of the sheath 10 is radiopaque marker 12 in the form of an interior tubular element. The tube-shaped radiopaque marker 12 is composed of a radiopaque material that is opaque to x-rays. The radiopaque marker 12 is generally defined by a body having a substantially cylindrical sidewall 38 with an inner surface 26 and an outer surface 24. Typically, the outer diameter at the outer surface 24 of the radiopaque marker 12 is approximately equal to the diameter of the inner wall 16 of the sheath 10. Thus, when the radiopaque marker 12 is placed within the sheath 10, substantially all of the outer surface 24 of the radiopaque marker 12 is in contact with of the inner wall 16 of the sheath 10.

As may also be seen in FIG. 1, an inner wall 26 of the radiopaque marker 12 may taper along its proximal end, forming a funnel-shaped annular wall 30. The annular wall 30 may assist in guiding leads, instruments, or other items inserted into the introducer sheath 12 to the distal tip 14 of the sheath 10. The radiopaque marker 12 may extend along any portion of the sheath 10 as desired, so long as the length and thickness of the radiopaque marker 12 is sufficient to be detected during typical fluoroscopy operations when viewed at various angles of exposure. Similarly, the distal end 32 of the radiopaque marker 12 may have a curved or shaped outer wall 34, the curve or shape generally corresponding to the form of the lumen 16 or inner wall of the sheath 10. By matching the shapes of the walls, a greater bonding surface between the radiopaque marker 12 and sheath 10 may be achieved.

Figure 2:
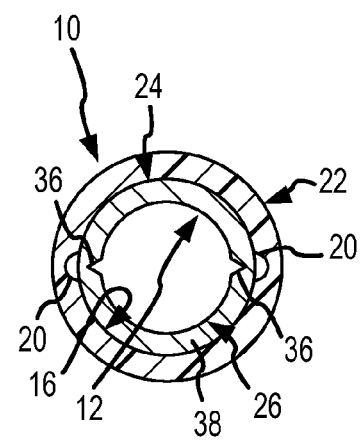
FIG. 2 depicts a cross-sectional view, taken along line 2-2 of FIG. 1, of the tip of the introducer sheath of FIG. 1.

FIG. 2 depicts a lateral cross-section of the splittable introducer sheath 10 shown in FIG. 1. The cross-section shown in FIG. 2 is taken along line 2-2 of FIG. 1. Generally, as depicted in FIG. 2, the radiopaque marker 12 and sheath 10 each include at least one area having a weakened or narrowed lateral cross-section, i.e., a marker score line 36 and a sheath score line 20, respectively.

The marker score lines 36 of the radiopaque marker 12 and the sheath score lines 20 of the sheath 10 are typically aligned with one another in order to facilitate splitting the radiopaque marker 12 in the same direction and along the same plane as the sheath 10. That is, the marker score lines 36 are typically within the plane defined by the sheath score lines 20. Further, the marker score lines 36 may extend only partially through the sidewall 38 of the radiopaque marker 12, as shown in FIG. 2, or may extend entirely therethrough. Where the marker score lines 36 extend completely though the radiopaque marker 12, the marker score lines 36 may abut the sheath score lines 20 formed on the inner sidewall 16 of the introducer sheath 10. Where the marker score lines 36 extend only partially through the sidewall 38 of the radiopaque marker 12, the marker score lines 36 may be on either the interior surface 26 or the exterior surface 24 of the radiopaque marker sidewall 38. FIG. 2 depicts the score lines along the interior surface 26 of the radiopaque marker sidewall 38.

Since the radiopaque marker 12 is bonded to a portion the interior wall 16 of the sheath 10, the radiopaque marker 12 and the longitudinal section of the sheath 10 enveloping the radiopaque marker 12 generally split substantially simultaneously.

Typically, regardless of whether the marker score lines 36 are along the interior surface 26 or the exterior surface 24 of the radiopaque tube 12, the marker score lines 36 and sheath score lines 20 are hollow, rather than filled in with a polymer or binding agent. In alternative embodiments, a binding material, polymer, or other element having a weaker resistance to shear stress created by splitting the sheath 10 along the sheath score line 20 may at least partially fill in one or more of the either the sheath score line 20 or the marker score lines 36.

The radiopaque marker 12 may be made of a variety of radiopaque materials. For example, the radiopaque marker 12 may be made of radiopaque particulate suspended or otherwise mixed in a polymerized substance, such as barium sulfate, an x-ray impenetrable metal, or any other radiopaque substance that may be bonded to the inner wall of the introducer sheath 10. As described in more detail below (in the section entitled "Method of Constructing a Cannula Having a Radiopaque Marker"), the bonding between the radiopaque marker 12 and the sheath 10 may be achieved through thermal, sonic, chemical, mechanical, or adhesive bonding, or any other bonding means known to those skilled in the art. The exact bonding means may vary, depending on the compositions of the radiopaque marker 12 and the sheath 10.

Sheath Having Radiopaque Marker Embedded in the Sheath Wall

Figure 3:
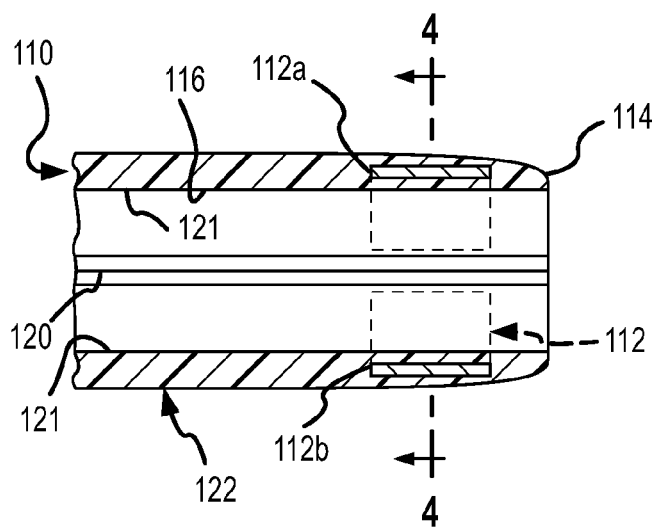
FIG. 3 depicts a longitudinal cross-sectional view of a tip of a second embodiment of a splittable introducer sheath incorporating a radiopaque marker formed of discrete elements.

FIG. 3 depicts a longitudinal cross-section of a second embodiment of a splittable introducer sheath 110 having a radiopaque marker 112 placed within its distal end 114. In the embodiment shown in FIG. 3, the radiopaque marker 112 comprises multiple, physically separate elements, instead of a unitary piece. Generally, the embodiment includes at least one piece of radiopaque material for each segment of the sheath wall 116, where a "segment" is defined as a portion of the sheath 110 extending between two score lines 120. Thus, where a sheath has two score lines (as is the case with the embodiment of FIG. 3), the radiopaque marker 112 may consist of two discrete radiopaque elements 112a, 112b. Where, for example, the sheath is divided into three pieces by three unique score lines (not shown), three discrete radiopaque elements may be embedded in the sheath walls.

Generally, it should be noted that a sheath and corresponding radiopaque marker may have any number of score lines, as necessary, to facilitate splitting of the sheath and radiopaque marker. For example, a sheath and radiopaque marker may each have four score lines, each offset by ninety degrees, to split the sheath and radiopaque marker into four pieces. Further, the sheath and radiopaque marker may have differing numbers of score lines. For example, a sheath may have two score lines, while the radiopaque marker used with the sheath may have twenty or thirty score lines. In such an embodiment, the plurality of score lines along the radiopaque marker may permit less precise alignment of any single score line with the sheath. If the radiopaque marker is scored every five millimeters along its circumference, for example, then the sheath score line will never be more than two and a half millimeters distant from the nearest radiopaque marker score line. Such distance between the sheath and marker score lines is sufficiently minimal to permit breaking of both the sheath and the radiopaque marker simultaneously. Accordingly, a radiopaque marker with this score pattern may be inserted within the sheath without reference to the sheath score lines.

In the present embodiment, the radiopaque marker 112 is typically embedded within the sidewall 116 of the sheath 110, rather than bonded to the interior surface 121 of the sheath 110, as with the embodiment of FIG. 1. Any of the shapes and configurations discussed herein, however, may be bonded to the interior surface 121 of the sidewall 116 of the sheath 110 and are suitable for use with the embodiment of FIG. 1. Likewise, the radiopaque marker 112 may be affixed to the exterior surface 122 of the sidewall 116 in alternative embodiments described below.

Still with reference to FIG. 3, a lateral cross-sectional view of the present embodiment of a distal tip 114 of the sheath 110 is depicted, showing the radiopaque marker portions 112a, 112b embedded in the sheath walls 116. The extension of each radiopaque marker portion 112a, 112b, along the wall of the introducer sheath 110 and terminating before the scored groove 120, is shown in phantom to aid in understanding the reach and extent of circumferential coverage of the radiopaque marker 12. Typically, the portion of the sheath sidewall 116 along which the scored groove 120 is formed does not contain any embedded radiopaque marker material. This lack of material along the scored groove 120 facilitates tearing and removal of the sheath 110 from a patient's body, without requiring the radiopaque marker 112 itself to be torn.

Figure 4:
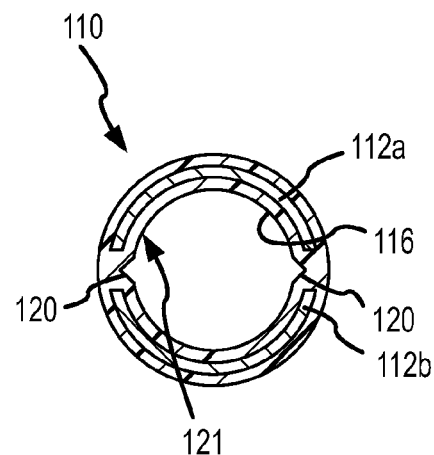
FIG. 4 depicts a cross-sectional view, taken along line 4-4 of FIG. 2, of the tip of the second embodiment of the introducer sheath, as shown in FIG. 3.

FIG. 4 displays a lateral cross-section of the distal tip 114 of the introducer sheath 110 of FIG. 3, taken along line 4-4 of FIG. 3. FIG. 4 more clearly shows the radiopaque marker 112 material embedded in the sheath walls 116, along with the lack of radiopaque marker material in the sheath sidewall 116 at the portions of the sidewall 116 having a scored groove 120.

FIG. 5 displays a sheath 110 having a first embodiment of a radiopaque marker 210. In this embodiment, the radiopaque marker 210 is again embedded in the sidewall 116 of the sheath. Here, however, the radiopaque marker 210 is generally of unitary construction, and extends throughout the sidewall 116 of the sheath 110, including running along the scored portion 120 of the sheath sidewall 116. The radiopaque marker 210 is generally ring-shaped.

In order to facilitate splitting the sheath 110, the present embodiment's radiopaque marker 210 may be grooved, scored, serrated, or provided with a sidewall having marker score lines 212 in the form of weakened or reduced material cross-sections generally corresponding to the location of the sheath score lines 120, grooves, or other splitting means running parallel to the longitudinal axis of the sheath 110. These various options are collectively referred to as "marker score lines" 212, and facilitate splitting the radiopaque marker 210. Generally, because the radiopaque marker 210 is embedded in the sidewall 116 of the sheath 110, the radiopaque marker 210 and a portion of the sheath 110 surrounding the radiopaque marker 210 are split substantially simultaneously. The alignment of the sheath score lines 120 and marker score lines 212 reduce the force necessary to split the distal tip 114 of the sheath. As with previously-discussed embodiments, the marker score lines 212 may be formed on either the interior surface 214 or exterior surface 216 of the radiopaque marker 210 sidewall. Generally, the depression or cavity 218 defined by the marker score lines 212 remains hollow, although alternative embodiments may at least partially fill in one or more of these marker score lines 212 with a binding material, polymer, or other element having a weaker resistance to shear stress created when splitting the sheath 110. The sheath score lines 120 may similarly be filled with a binding material, polymer, or other element having a weaker resistance to shear stress than the material forming the sheath 110 if desired.

In alternative embodiments, a series of overlapping or closely spaced contiguous radiopaque markers may be used, instead of a single radiopaque marker ring 210. In such an embodiment, the radiopaque markers lying in a plane defined by a line connecting the sheath score lines 120 may be scored or grooved as described above. In other words, radiopaque markers embedded in the sheath sidewall 116 directly behind the score lines 120 may also be scored or have a reduced cross-section.

FIG. 6 depicts a lateral cross-section of the sheath 110 of FIG. 5, taken along line 6-6 of FIG. 5. The alignment of the score lines 120 on the interior surface 121 of the sidewall 116 with the score lines 212 on the radiopaque marker 210 is shown. Although the radiopaque marker 210 is shown as scored along its interior sidewall 214, the exterior sidewall 216 of the radiopaque marker 210 may alternatively be scored, or both sidewalls may be scored.

FIG. 7 depicts a cross-sectional view of the tip 114 of a splittable introducer sheath 110 incorporating another embodiment of a radiopaque marker 310. The radiopaque marker 310 embedded in the sheath 110, as shown in FIG. 7, is not grooved or scored longitudinally. Instead, a V-shaped notch 312 is formed in the radiopaque marker 310 along opposing sections corresponding to the sheath score lines 120. Accordingly, the amount of radiopaque marker 310 material resisting splitting of the sheath 110 along the score lines 120 is minimized. In turn, this permits easier splitting of the sheath 110 and radiopaque marker 310.

Many different notch shapes may be incorporated into the annular radiopaque marker 310, several of which are discussed below with respect to FIGS. 8-12. It should be noted that, for each of the radiopaque markers discussed, the notch 312 generally underlies or is located co-planarly with at least one sheath score line 120. For each of these radiopaque markers, the lack of radiopaque material in the notch formed is insufficient to significantly impact the overall opacity of the radiopaque marker during fluoroscopy or other exploratory procedures.

FIG. 8 depicts a lateral, cross-sectional view of the sheath tip 114 of FIG. 7, taken along line 8-8 of FIG. 7 through the notch 312. The lack of radiopaque material underlying or adjacent to the sheath score line 120 is clearly shown at the cross-section. Were the cross-section taken closer to the distal end of the radiopaque marker 310, the radiopaque material of the present embodiment would form a continuous ring. The notch 312 in the radiopaque marker 310 of FIGS. 7 and 8 generally terminates in a point 314.

Figure 9:
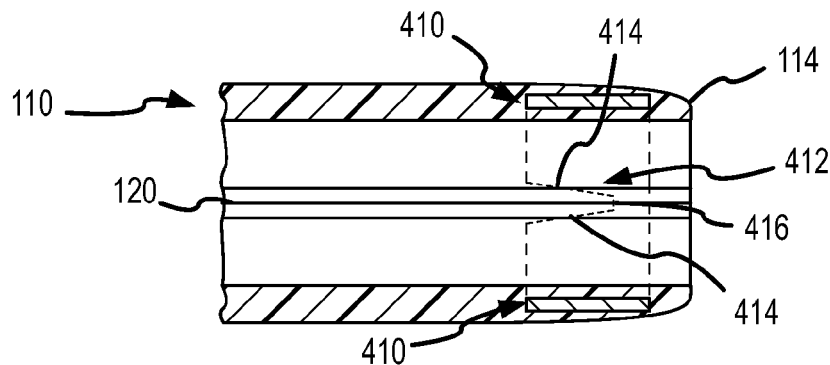
FIG. 9 depicts a cross-sectional view of a tip of a splittable introducer sheath incorporating a third embodiment of a radiopaque marker ring.

FIG. 9 depicts a longitudinal, cross-sectional view of the distal portion 114 of a splittable introducer sheath 110 incorporating a third embodiment of a radiopaque marker 410. It should be noted that the embodiment discussed with respect to FIGS. 1 and 2 is a hollow plug. Similarly, in the embodiment shown in FIGS. 3 and 4, the radiopaque marker 112 is made of separate pieces 112a, 112b. Accordingly, the embodiment shown in FIGS. 5 and 6 is the first embodiment depicting the radiopaque marker 310 as a ring. FIGS. 7 and 8 depict a second ring embodiment, and FIG. 9 depicts a third ring embodiment. In FIG. 9, the notch 412 has sloped walls 414. These walls terminate in a substantially flat surface 416 parallel to the distal end of the marker ring instead of coming to a point, as in the embodiment of FIGS. 7 and 8.

Figure 10:
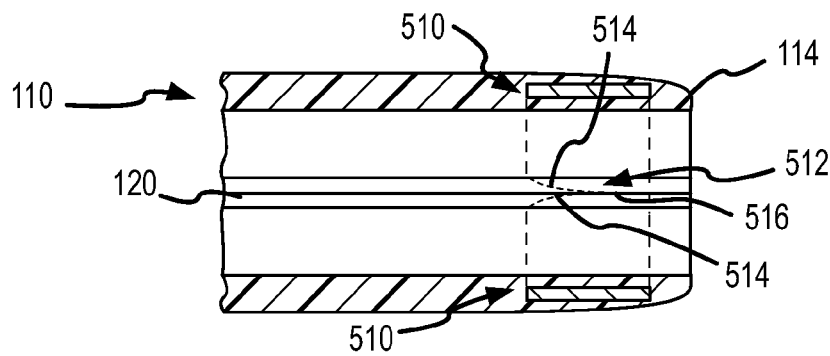
FIG. 10 depicts a cross-sectional view of a tip of a splittable introducer sheath incorporating a fourth embodiment of a radiopaque marker ring.

FIG. 10 depicts a longitudinal, cross-sectional view of the distal portion 114 of a splittable introducer sheath 110 incorporating a fourth embodiment of a radiopaque marker 510. In this embodiment, the notch 512 has inwardly curved sidewalls 514 (i.e., sidewalls curving towards the center of the notch 512). The notch sidewalls 514 meet at a point 516, but may terminate in a flat or curved surface in alternate embodiments.

Figure 11:
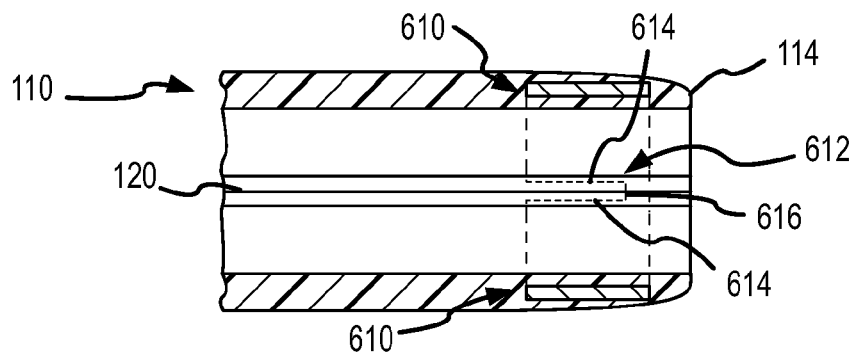
FIG. 11 depicts a cross-sectional view of a tip of a splittable introducer sheath incorporating a fifth embodiment of a radiopaque marker ring.

FIG. 11 depicts a longitudinal, cross-sectional view of the distal portion 114 of a splittable introducer sheath 110 incorporating a fifth embodiment of a radiopaque marker 610. The embodiment of FIG. 11 includes a radiopaque marker 610 having a notch 612 with parallel sidewalls 614 and a base wall 616 perpendicular to the sidewalls 614. As with the embodiments discussed with respect to FIGS. 7-10, the lack of radiopaque material along the notch 612 facilitates splitting of the sheath along the sheath score line 120.

Figure 12:
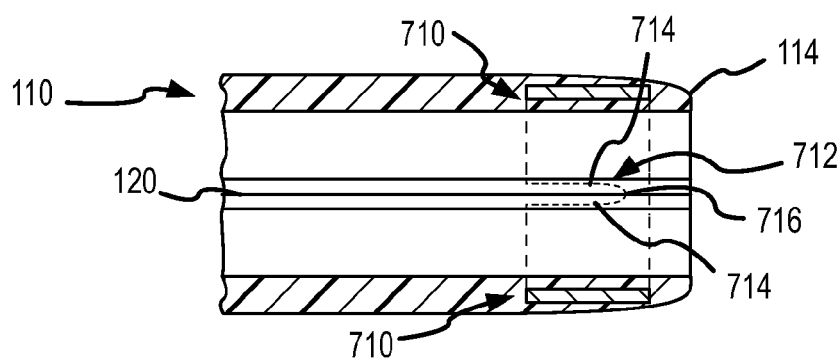
FIG. 12 depicts a cross-sectional view of a tip of a splittable introducer sheath incorporating a sixth embodiment of a radiopaque marker ring.

FIG. 12 depicts a longitudinal cross-sectional view of the distal portion 114 of a splittable introducer sheath 110 incorporating a sixth embodiment of a radiopaque marker ring 710. Although this embodiment of the marker ring includes substantially parallel notch 712 sidewalls 714, like those shown in FIG. 11, the marker ring of FIG. 12 has a curved base wall 716 instead of a flat one 616.

Figure 13:
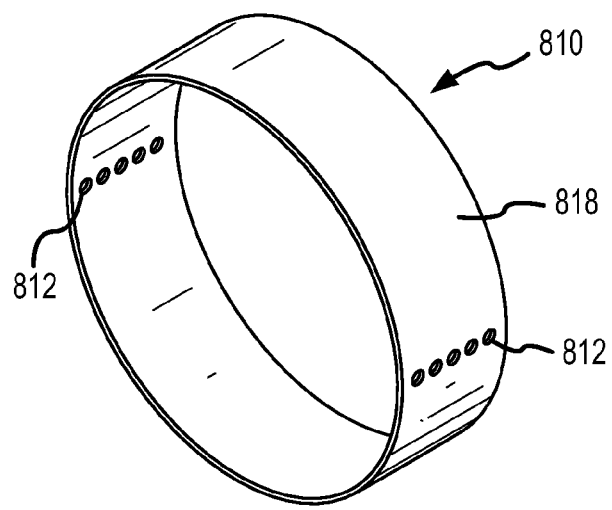
FIG. 13 is an isometric view of a radiopaque marker according to a seventh embodiment of the invention.
Figure 14:
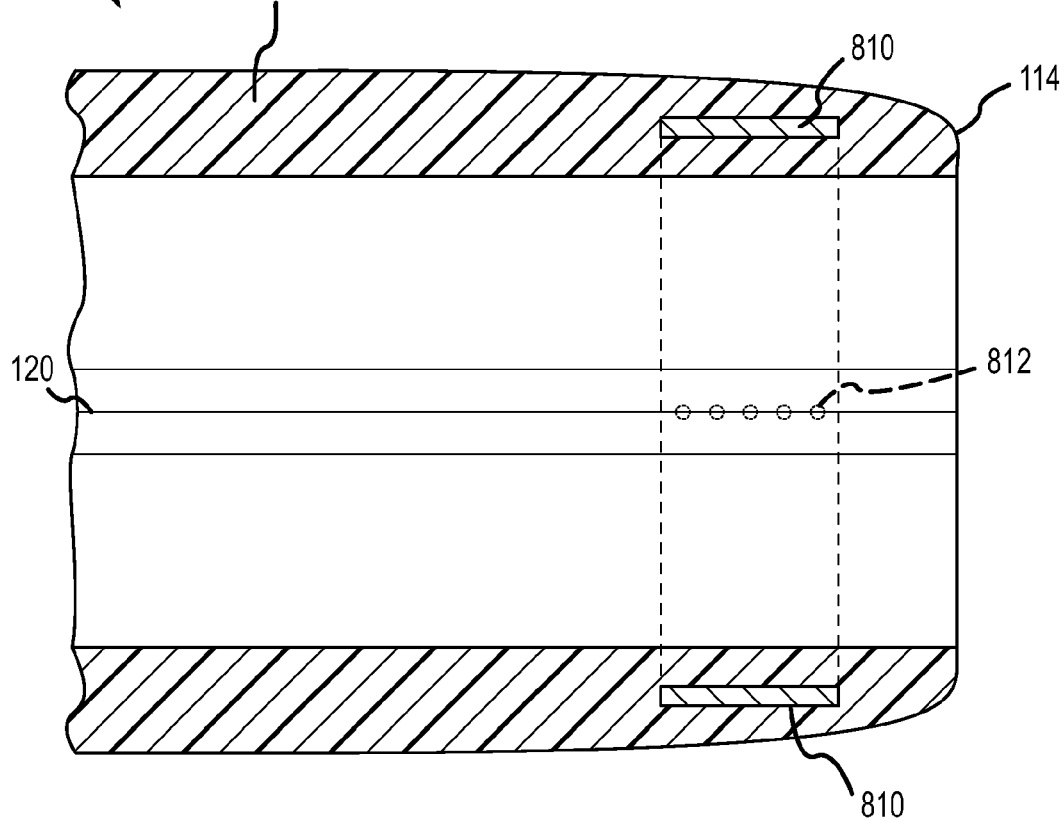
FIG. 14 is a cross-section view of the radiopaque marker of FIG. 13 embedded in the tip of a splittable introducer sheath.

FIGS. 13 and 14 depict another embodiment of a radiopaque marker 810 according to the present invention. In this embodiment the radiopaque marker 810 is generally a solid band of radiopaque material, for example, platinum or a platinum and iridium alloy. The radiopaque marker 810 is weakened on opposing sides by the provision of a series of apertures 812 formed within the sidewall 818 of the radiopaque marker 810 in a longitudinal arrangement. One advantage of this design is the efficiency gained in the manufacturing process because the need to longitudinally orient the radiopaque marker 810 for insertion into the tip 114 of the sheath 110 is obviated. The apertures 812 may be formed, for example, by using a laser to drill holes into the wall of the radiopaque marker 810, first on one side and then on an opposing side. As shown in FIG. 14, the radiopaque marker 810 is embedded in the sidewall 116 of the sheath 110 near the tip 114 in a process further described below. The apertures 812 are aligned with the score lines 120 of the sheath 110, whereby when the sheath 110 is separated, the radiopaque marker 810 weakened by the apertures 812 may be likewise be torn into halves. With this design, only a modicum of force is needed to tear the radiopaque marker 810. For example, a radiopaque marker 810 of the design of FIGS. 13 and 14 of 0.125 in. diameter was found to separate upon the application of between 1.2 and 2 ft-lbs of force.

Figure 15:
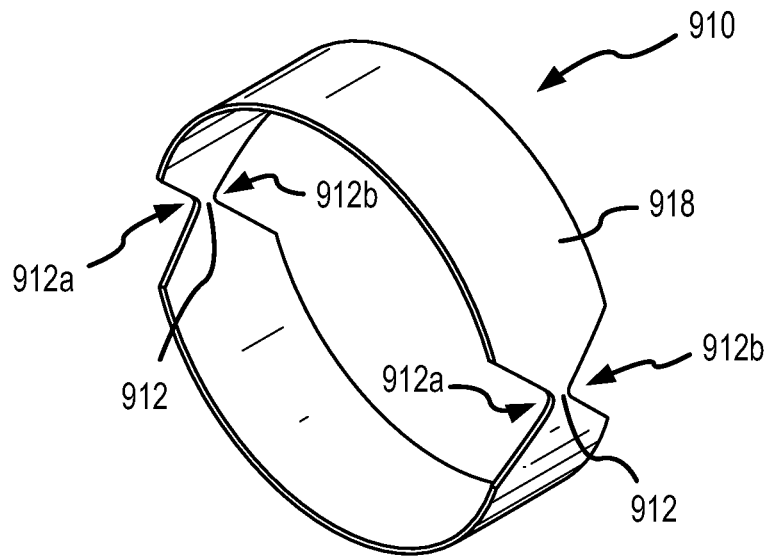
FIG. 15 is an isometric view of a radiopaque marker according to an eighth embodiment of the invention.
Figure 16:
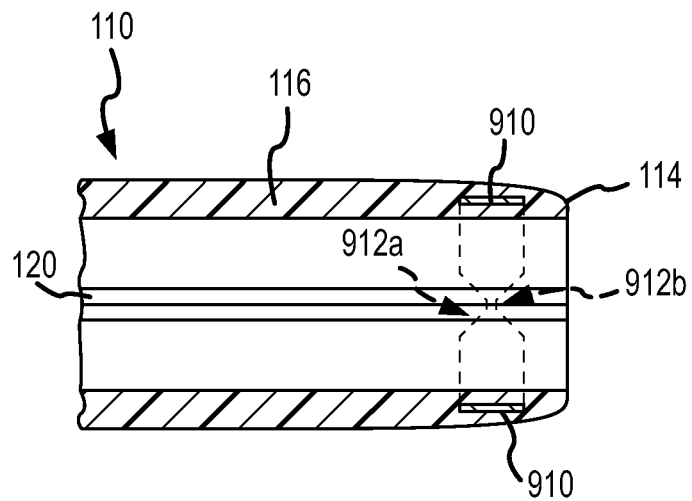
FIG. 16 is a cross-section view of the radiopaque marker of FIG. 15 embedded in the tip of a splittable introducer sheath.

A further embodiment of a radiopaque marker 910 according to the present invention is depicted in FIGS. 15 and 16. The radiopaque marker 910 is again generally a solid band of radiopaque material. In this embodiment, the radiopaque marker 910 is weakened on opposing sides by pairs of notches 912a, 912b on the proximal and distal sides of the radiopaque marker 910 forming a "double-V" shape on opposing sides of a connecting strip 912. The sidewall 918 of the radiopaque marker 910 is a continuous band as the apexes of the notches 912a, 912b do not meet. The opposing sides of the sidewall 916 exhibit an "hourglass" shape at the location of the notches 912a, 912b. Similar to the embodiment of FIGS. 13 and 14, an advantage of this design is the efficiency gained in the manufacturing process because the need to longitudinally orient the radiopaque marker 910 for insertion into the tip 114 of the sheath 110 is obviated. As shown in FIG. 16, the radiopaque marker 910 is embedded in the sidewall 116 of the sheath 110 near the tip 114 in a process further described below. The notches 912a, 912b are aligned with the score lines 120 of the sheath 110, whereby when the sheath 110 is separated, the radiopaque marker 910 weakened at the connecting strip 912 by the notches 912a, 912b may be likewise be torn into halves. An additional advantage of the design of this embodiment is that after the sheath 110 and radiopaque marker 910 are split in half, each of the halves of the radiopaque marker 910 is firmly retained within the sidewall 116 of the sheath 110 by the sheath material that fuses together in the area of the notches 912a, 912b during the manufacturing process as further described below.

Figure 17:
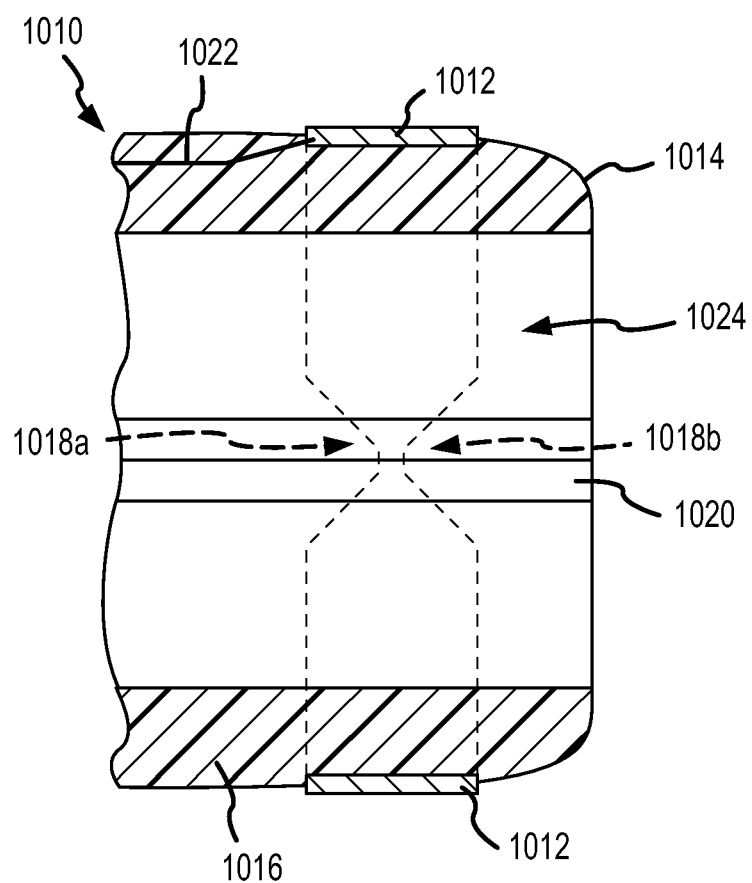
FIG. 17 is a cross-section view of a radiopaque marker electrode according to an ninth embodiment of the invention attached about the tip of a catheter.
Figure 18:
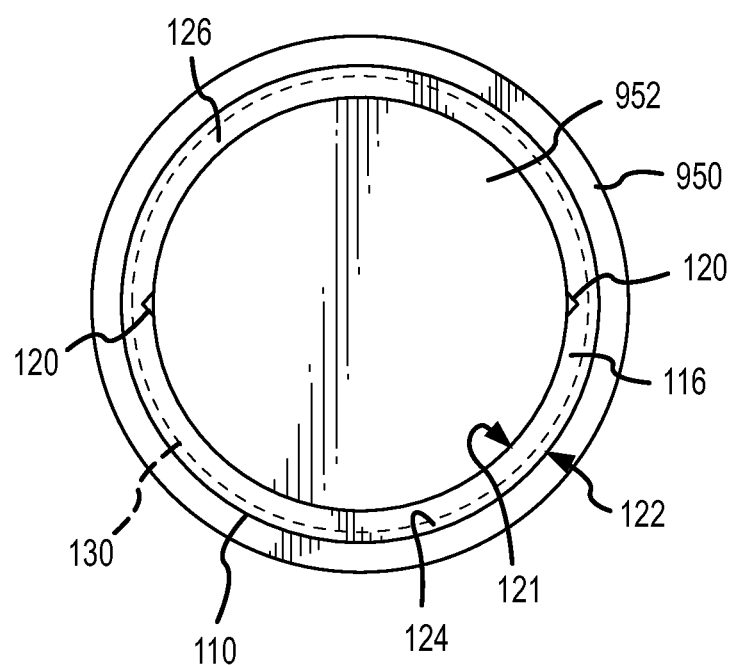
FIG. 18 is a plan view of a splittable introducer sheath held between an inner mandrel and an outer holding die to aid in the insertion of a cutting die to create an annular incision for embedding a radiopaque marker.

FIG. 17 depicts an alternative embodiment of the present invention. In this embodiment, a splittable catheter 1010 is includes a radiopaque marker electrode 1010 about the outer diameter of the distal tip 1014 of the splittable catheter 1010. Such a splittable catheter 1010 may be used to ablate tissue within the vasculature or other cavities of a patient. The radiopaque marker electrode 1012 is generally a solid band of radiopaque material that also acts as an electrode. In this embodiment, the radiopaque marker electrode 1012 is weakened on opposing sides by pairs of notches 1018a, 1018b on the proximal and distal sides of the radiopaque marker electrode 1012 forming a "double-V" shape. The sidewall of the radiopaque marker 1012 is a continuous band as the apexes of the notches 1018a, 1018b do not meet. The opposing sides of the sidewall exhibit an "hourglass" shape at the location of the notches 1018a, 1018b. The notches 1018a, 1018b are aligned with the score lines 1020 of the splittable catheter 1010, whereby when the splittable catheter 1010 is separated, the radiopaque marker 1012 weakened by the notches 1018a, 1018b may be likewise be torn into halves.

The radiopaque marker electrode 1012 may be attached or adhered to the outer diameter of the splittable catheter 1010 using adhesive, swaging, thermal, or ultrasonic bonding techniques. The radiopaque marker electrode 1012 may also be recessed into an annular band in the sidewall 1016 of the splittable catheter 1010 as shown in order to ensure a strong bond between the radiopaque marker electrode 1012 and the splittable catheter 1010.

As depicted in FIG. 17, a lead 1022 is embedded in the sidewall 1016 of the splittable catheter 1010 and connected with the radiopaque marker electrode 1012 to supply energy from an energy source to the radiopaque marker electrode 1012. Alternately, the lead 1022 may be trained through the lumen 10242 of the catheter 1010 and embedded in the sidewall 1016 of the catheter 1010 only at the distal tip 1014 of the catheter 1010 adjacent the radiopaque marker electrode 1012 (not shown). A separate lead 1022 may be provided for each half of the radiopaque marker electrode 1012 to operate as a bipolar electrode or to maintain electrical connection with both halves after the radiopaque marker electrode 1012 is split.

It should be noted that the various embodiments of the sheath 10 and radiopaque marker 12 discussed herein, and depicted in the various figures, may have a variety of measurements, either standing alone or in relation to one another. For example, the thickness of the sheath sidewall 16 and/or radiopaque marker 12 may vary from embodiment to embodiment, as may the diameter of the lumen. Accordingly, the embodiments shown in the figures are for illustrative purposes only, and should not be construed as depicting exact measurements or relationships between the sizes of various elements of the present invention.

Method of Constructing a Sheath Having a Radiopaque Marker

The general procedure for constructing a splittable sheath 10 including a radiopaque marker 12 designed to facilitate sheath splitting according to the embodiment shown in FIGS. 1 and 2, although it should be understood that this method of construction is generally applicable to all embodiments discussed herein. Initially, the splittable sheath 10 tubing is extruded and scored. Next, a radiopaque marker 12 may be inserted into the distal end 14 of the sheath lumen before forming the sheath tip. Once the radiopaque marker 12 is lodged within the tip 14, the sheath tip 14 and radiopaque marker 12 may be inserted into a tip forming die.

In more detail, a die pin or rod may be run along the length of the sheath 10 from its proximal end to its distal end 14. Generally, the die pin is circular in cross-section, approximately equal in diameter to the diameter of the interior wall 16 of the sheath 10, and has opposing, outwardly-extending projections. As these projections run along the interior sheath sidewall 16, they score the sidewall 16, thus creating the score lines 20 previously referenced. As the die pin passes to the distal end 14 of the sheath 10, it also scores the radiopaque marker 12.

Where the sheath score lines 20 and marker score lines 36 are not immediately adjacent (for example, as shown in FIG. 2), both the sheath 10 and radiopaque marker 12 may be scored prior to inserting the radiopaque marker 12 into the sheath 10.

Once the scoring process is complete and the radiopaque marker 12 is snugly nested in the sheath 10, the radiopaque marker 12 and sheath 10 may be bonded. Exemplary bonding methods include thermal, sonic, and chemical bonding.

Finally, the sheath tip 14 is formed. The sheath tip 14 may be formed by injecting or extruding additional polymer material, deforming via heat or mechanical means a portion of the sheath 10, overmolding additional polymer material in the shape of the tip 14, and so forth. If the tip 14 is overmolded, the overmold material may be deposited around a portion of the sheath 10, or alternatively the radiopaque marker 12 may be only partially inserted into the sheath 10 and the overmold material placed around the radiopaque marker 12.

Yet another manufacturing method is particularly suitable for creating the embodiments discussed with respect to FIGS.

3-12. First, a splittable sheath 110 having a radiopaque marker 112 may be made by extruding the sheath 110, as described above. The sheath 110 may be held between a holding die 950 about the exterior surface 122 and a mandrel pin within the lumen of the sheath 110 against the interior surface 121. The extruded sheath 110 may be slit longitudinally, to create an annular slit 130 beginning at the sheath's distal end 114 and extending along a portion of the sheath sidewall 116. The annular slit 130 is typically circular in lateral cross-section, and divides the distal end 114 of the sheath 110 into an inner ring 126 and outer ring 124. In order to form the annular slit 130, a cutting die (not shown) with an annular cutting edge may be impressed into the sidewall 116 of the sheath 110 at the distal tip 114. The holding die 950 and the mandrel pin 952 maintain the form of the sheath 110 and prevent the distal tip 114 of the sheath 110 from deflecting under the force of the cutting die. The depth of the score lines 120 in the interior surface 116 of the sidewall 116 of the sheath 110 is approximately one-third the radial thickness of the sidewall 116. The annular slit 130 is positioned approximately one-third the radial thickness of the sidewall 116 from the outer surface 122 of the sheath 110. In this manner, the annular slit 130 is positioned halfway between the apex of the score lines 120 and the outer surface 122 of the sheath 110, thereby maintaining the integrity of the inner ring 126 of the sidewall 116.

The radiopaque marker 112 (or its constituent elements 112a, 112b) may then be inserted into the annular slit 130, effectively being placed between the inner ring 126 and outer ring 124 of polymer material at the distal tip 114 of the sheath 110. The inserted radiopaque marker may be made of strips, braided material, a solid ring such as those discussed with respect to FIGS. 5-12, or separate pieces such as those discussed with respect to FIGS. 3 and 4. Generally, the radiopaque marker 112 is placed inside the sheath 110 in such a manner that the marker scores, serrations, notches, reduced cross-sectional areas, and so forth align with the sheath score lines 120. In alternative embodiments employing a multi-serration or multi-score radiopaque marker, the exact alignment of marker and sheath score lines may not be necessary. The radiopaque marker 112 is typically inserted far enough into the sheath 110 that it is entirely encapsulated by the sidewall 116 of the sheath 110, although alternative embodiments may vary this procedure.

Once the radiopaque marker 112 is properly positioned, the inner ring 124 and outer ring 124 of the sheath 110 may be thermally or chemically bonded to one another to seal the radiopaque marker 112 inside the sheath 110. The tip 114 may then be formed as previously discussed, or the bonding process may simultaneously form the tip 114. The distal tip 114 may be formed as an atraumatic tip with a rounded radius to reduce the potential for causing tissue damage.

Figure 19:
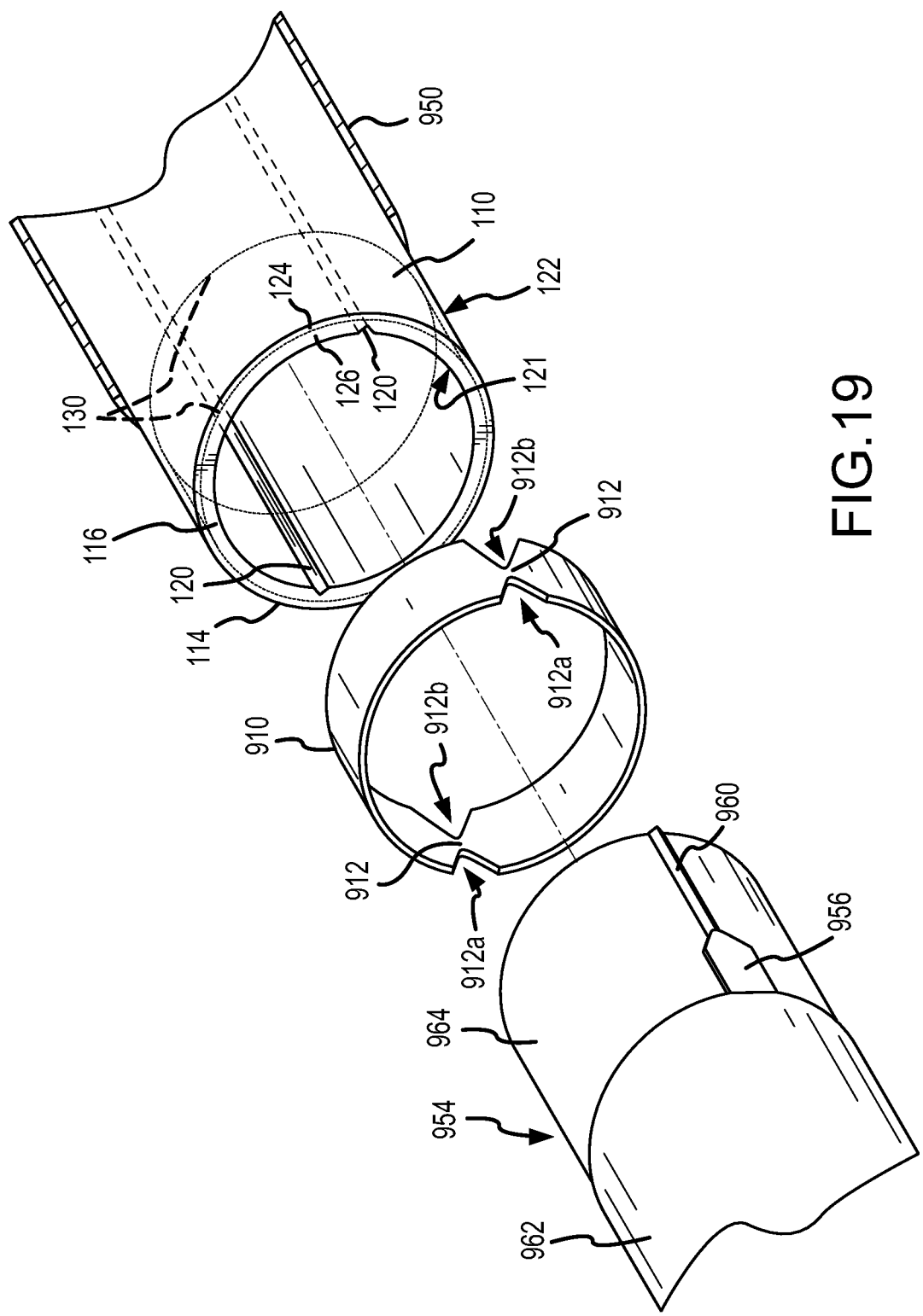
FIG. 19 is an isometric view of an insertion tool, a radiopaque marker, a splittable introducer sheath (in partial cross-section), and a holding die.
Figure 20:
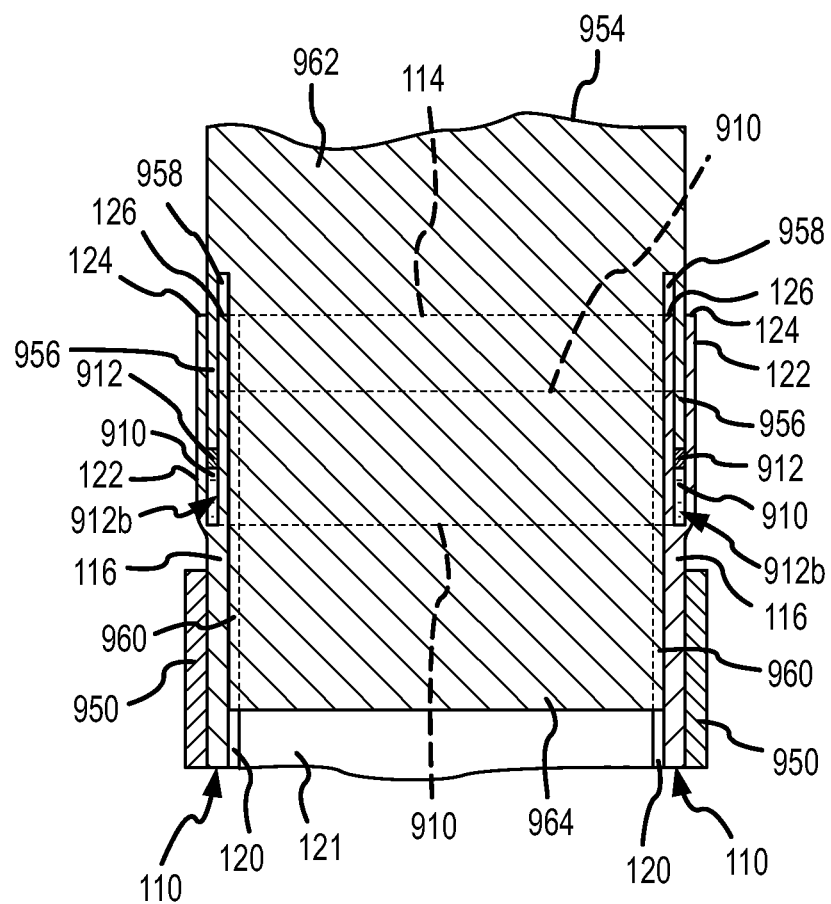
FIG. 20 is a cross-section view of the insertion tool, radiopaque marker, splittable introducer sheath, and holding die of FIG. 19 with the radiopaque marker inserted into the tip of the sheath.

In one embodiment, the radiopaque marker is particularly susceptible to mechanical insertion techniques. FIGS. 19 and 20 depict a process for inserting the radiopaque marker 910 of FIGS. 15 and 16 into the distal tip 114 of a sheath 110. Because the radiopaque marker 910 has identical notches 912a, 912b on either side of the narrow connecting strip 912, there is no requirement for a particular longitudinal orientation of the radiopaque marker 910 for insertion into the annular slit 130 as in other embodiments, for example, the embodiments of FIGS. 9-12 with single notches. The radiopaque marker 910 is longitudinally symmetric and may be inserted into the annular slit 130 with either end leading.

A specialized insertion tool 954 may be used to easily insert the radiopaque marker 910 into the annular slit 130 within the sheath 110 and align the notches 912a, 912b with the score lines 120 in the sheath 110. The insertion tool 954 is formed with a proximal section 962 and a distal section 964. The diameter of the distal section 964 is slightly smaller than the inner diameter of the sheath 110 defined by the inner surface 121. The proximal section 962 may be of slightly larger diameter than the distal section 964. The distal section 964 is additionally formed with a pair of score guides 960 adapted to fit within the score lines 120 of the sheath 110. A pair of marker guides 956 extend distally from the proximal section 962 of the insertion tool 954 and are spaced apart from the distal section by gaps 958. Each marker guide 956 is aligned with a respective score guide 960 on an opposing side of the insertion tool 954. The score guides 960 may extend underneath the marker guides 956 in the gaps 958 between the marker guides 956 and the distal section 964. In this design, space still remains between the marker guides 956 and the score guides 960. The diameter of the insertion tool 954 as measured between the marker guides 956 is the same as the diameter of the radiopaque marker 910. Similarly, the diameter of the radiopaque marker 910, and thus the diameter of the insertion tool 954 at the position of the marker guides 956, is the same as the diameter of the annular slit 130 in the sheath 110. Each marker guide 956 has a pointed distal end that is sized to engage an opposing notch 912a (or 912b depending upon the orientation of the radiopaque marker 912) in the radiopaque marker 912.

To insert the radiopaque marker 910 into the sheath 110, the radiopaque marker 910 is placed over the distal section 964 of the insertion tool and the notches 912a are engaged by the marker guides 956. The score guides 960 on the distal section 964 of the insertion tool 954 are then aligned with the score lines in the sidewall 116 of the sheath 110. The distal section 964 of the insertion tool 954 is inserted into the lumen of the sheath 110 and the radiopaque marker 910 is simultaneously inserted into the annular slit 130 between the outer ring 124 and the inner ring 126. In this manner, the notches 912a, 912b of the radiopaque marker are aligned with the score lines 120 upon insertion of the radiopaque marker 910 into the annular slit 130. The gap 958 between the marker guides 956 and the distal section 964 of the insertion tool 954 allows the inner ring 126 to slide between the marker guides 956 and the distal section 964 during the insertion process.

A holding die 950 may provide support to the sheath 110 and the distal section 964 of the insertion tool may extend within the holding die 950 during the insertion process. It may be preferred that the holding die 950 not extend to the distal tip 114 of the sheath 110 to allow sufficient room for expansion of the sidewall 116 upon insertion of the radiopaque marker 910 into the sheath 110. The larger diameter of the proximal section 962 may be provided to limit the depth of insertion of the radiopaque marker 910 into the sheath 110 by engaging the distal tip 114 of the sheath 110.

In one embodiment, the marker guides 956 may be magnetized to attract and hold the radiopaque marker 910 in position about the insertion tool 954 during the insertion process. The marker guides 956 may be electromagnetic, whereby the magnetic force on the radiopaque marker 910 is released once the radiopaque marker 910 is fully inserted in the annular slit 130. This may ensure that the radiopaque marker 910 remains in place while the insertion tool 954 is removed from the sheath 110.

As in previous embodiments, once the radiopaque marker 910 is inserted in the sheath 110 and the insertion tool 954 is removed, the inner ring 126 and outer ring 124 of the sheath 110 may be thermally or chemically bonded to one another to seal the radiopaque marker 112 inside the sheath 110. Bonding between the inner ring 126 and outer ring 124 in the area of the notches 112a, 112b ensures that the radiopaque marker 910 is held firmly in place, both rotationally and longitudinally, even after the sheath 110 is ultimately split. The bonding process may simultaneously form the distal tip 114 with an atraumatic rounded radius to reduce the potential for causing tissue damage.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular examples or embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A splittable sheath having a distal end opaque to x-rays, the splittable sheath comprising:
   a sheath body including a pair of longitudinally extending weakened portions running substantially along a length of the sheath body; and
   a contiguous radiopaque ring located at a distal end of the sheath body and comprising a pair of weakened areas that permit the contiguous radiopaque ring to be broken into at least two discrete pieces when the sheath body is torn along the pair of longitudinally extending weakened portions,
   wherein one of the longitudinally extending weakened portions is aligned with one of the weakened areas and the other of the longitudinally extending weakened portions is aligned with the other of the weakened areas.

2. The splittable sheath according to claim 1, wherein the distal end of the sheath body is separated into an inner ring and an outer ring via a longitudinal cut around its perimeter, and wherein the contiguous radiopaque ring is sealed inside the distal end of the sheath body between the inner ring and the outer ring.

3. The splittable sheath according to claim 1, wherein the contiguous radiopaque ring further comprises a tubular body having an inner surface and an outer surface, and wherein the inner surface of the tubular body is formed in a funnel shape at a proximal end thereof.

4. The splittable sheath according to claim 1, wherein each of the longitudinally extending weakened portions comprises a score line.

5. The splittable sheath according to claim 1, wherein the pair of longitudinally extending weakened portions comprises a pair of grooves spaced apart from each other.

6. The splittable sheath according to claim 5, wherein the contiguous radiopaque ring further comprises an annular wall, and wherein
   one of the weakened areas comprises a first pair of notches in the annular wall at a first position on the annular wall, wherein each of the first pair of notches extends from an opposing longitudinal end of the annular wall and is separated from the other by a first connecting strip; and
   the other of the weakened areas comprises a second pair of notches in the annular wall at a second position on the annular wall spaced apart from the first position, wherein each of the second pair of notches extends from an opposing longitudinal end of the annular wall and is separated from the other by a second connecting strip; and
   wherein the first pair of notches is aligned with a first one of the grooves and the second pair of notches is aligned with a second one of the grooves.

7. The splittable sheath according to claim 6,
   wherein each notch in the first pair of notches, and likewise each notch in the second pair of notches, defines an apex;
   wherein each apex of the first pair of notches opposes the other on opposite sides of the first connecting strip; and
   wherein each apex of the second pair of notches opposes the other on opposite sides of the second connecting strip.

8. The splittable sheath according to claim 6, wherein the sheath body is a tubular body formed by a sidewall, wherein each of the pair of grooves is positioned on an interior surface of the sidewall.

9. The splittable sheath according to claim 1, wherein the sheath body is a tubular body formed by a sidewall, wherein the contiguous radiopaque ring is positioned on an exterior surface of the sidewall.

10. The splittable sheath according to claim 1, further comprising an electrode lead coupled to the contiguous radiopaque ring.

11. The splittable sheath according to claim 1, wherein each of the pair of longitudinally extending weakened portions is spaced substantially opposite each other and each of the pair of weakened areas is spaced substantially opposite each other.

12. The splittable sheath according to claim 1, wherein each of the pair of longitudinally extending weakened portions is diametrically opposite the other and each of the pair of weakened areas is diametrically opposite the other.

13. The splittable sheath according to claim 1, wherein the pair of longitudinally extending weakened portions comprises a pair of grooves spaced apart from each other, and wherein each of the weakened areas comprises a marker score line.

14. The splittable cannula according to claim 1, wherein the sheath body is a tubular body formed by a sidewall, and wherein an exterior surface of the sidewall defines an annular recessed band and the contiguous radiopaque ring is positioned within the annular recessed band.

15. The splittable sheath according to claim 1, wherein the pair of weakened areas divide the contiguous radiopaque ring into substantially equal opposing halves, and wherein the contiguous radiopaque ring further comprises at least one connecting strip in each of the weakened areas joining the opposing halves of the contiguous radiopaque ring.

16. The splittable cannula according to claim 15, wherein
   one of the weakened areas further comprises a first plurality of holes within the contiguous radiopaque ring extending longitudinally at a first position on the contiguous radiopaque ring;

the other of the weakened areas further comprises a second plurality of holes within the contiguous radiopaque ring extending longitudinally at a second position on the contiguous radiopaque ring substantially opposite the first position;

the at least one connecting strip comprises a plurality of connecting strips; and each of the first and second pluralities of holes is separated from an adjacent hole by a respective one of the plurality of connecting strips.

17. A splittable catheter having a distal end opaque to x-rays, the splittable catheter comprising:

a tubular body formed by a sidewall, wherein the sidewall further defines a pair of grooves spaced apart from each other and extending longitudinally along the tubular body;

a radiopaque marker electrode attached to an outer surface of the sidewall and positioned at the distal end of the splittable catheter, the radiopaque marker electrode having an annular wall;

a first pair of notches in the annular wall at a first position on the annular wall, wherein each of the first pair of notches extends from an opposing longitudinal end of the annular wall, terminates in an apex, and is separated from the other by a first connecting strip; and a second pair of notches in the annular wall at a second position on the annular wall spaced apart from the first position, wherein each of the second pair of notches extends from an opposing longitudinal end of the annular wall, terminates in an apex, and is separated from the other by a second connecting strip;

wherein the first pair of notches is aligned with a first one of the grooves and the second pair of notches is aligned with a second one of the grooves; and an electrode lead coupled to the radiopaque marker electrode.

* * * * *